United States Patent [19]

Bromidge et al.

[11] Patent Number: 5,356,914
[45] Date of Patent: Oct. 18, 1994

[54] 1,2,5,6-TETRAHYDROPYRIDINE OXIME DERIVATIVES

[75] Inventors: Steven M. Bromidge; Barry S. Orlek; Steven Dabbs, all of Harlow, England

[73] Assignee: Beecham Group p.l.c., England

[21] Appl. No.: 39,156

[22] PCT Filed: Oct. 9, 1991

[86] PCT No.: PCT/GB91/01751
  § 371 Date: Apr. 5, 1993
  § 102(e) Date: Apr. 5, 1993

[87] PCT Pub. No.: WO92/06959
  PCT Pub. Date: Apr. 30, 1992

[30] Foreign Application Priority Data
  Oct. 12, 1990 [GB] United Kingdom ............. 9022232.4
  Mar. 27, 1991 [GB] United Kingdom ............. 9106490.7

[51] Int. Cl.$^5$ .................. C07D 213/89; A61K 31/44
[52] U.S. Cl. ........................... 514/354; 514/357;
  546/14; 546/326; 546/330; 546/331; 546/332;
  546/335; 546/336; 546/337; 546/338
[58] Field of Search ............... 546/332, 334, 335, 14,
  546/326, 330, 331, 336, 337, 338; 514/357, 354

[56] References Cited

U.S. PATENT DOCUMENTS

| | | | |
|---|---|---|---|
| 4,710,508 | 12/1987 | Bergmeier et al. ................ | 514/357 |
| 4,786,648 | 11/1988 | Bergmeier et al. ................ | 514/357 |
| 4,798,841 | 1/1989 | Downs ............................. | 514/357 |
| 4,927,837 | 5/1990 | Galliani et al. .................. | 514/331 |
| 4,937,239 | 6/1990 | Lauffer et al. ................... | 514/183 |
| 5,015,655 | 5/1991 | Galliani et al. .................. | 514/413 |
| 5,110,828 | 5/1992 | Bromidge et al. ................. | 514/413 |

FOREIGN PATENT DOCUMENTS

| | | |
|---|---|---|
| 0094742 | 11/1983 | European Pat. Off. ............. 514/413 |
| 0239445 | 9/1987 | European Pat. Off. ............. 514/357 |
| 0257741 | 3/1988 | European Pat. Off. ............. 514/413 |
| 0261763 | 3/1988 | European Pat. Off. ............. 514/413 |
| 0271798 | 6/1988 | European Pat. Off. ............. 514/357 |
| 0287356 | 10/1988 | European Pat. Off. ............. 514/413 |
| 0288394 | 10/1988 | European Pat. Off. ............. 514/357 |
| 0291673 | 11/1988 | European Pat. Off. ............. 514/357 |
| 0308283 | 3/1989 | European Pat. Off. ............. 514/357 |
| 0308284 | 3/1989 | European Pat. Off. ............. 514/357 |
| 0338723 | 10/1989 | European Pat. Off. ............. 514/357 |
| 0316718 | 12/1989 | European Pat. Off. ............. 514/413 |
| 0366561 | 5/1990 | European Pat. Off. ............. 514/413 |
| 0392803 | 10/1990 | European Pat. Off. ............. 514/413 |

*Primary Examiner*—C. Warren Ivy
*Assistant Examiner*—Zinna N. Davis
*Attorney, Agent, or Firm*—Linda E. Hall; Stuart R. Suter; Edward T. Lentz

[57] ABSTRACT

Compounds of formula (I) or a pharmaceutically acceptable salt thereof:

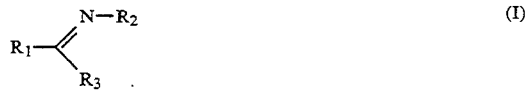

wherein $R_1$ represents a 1,2,5,6-tetrahydropyridin-3-yl group N-substituted by $R_{10}$ wherein $R_{10}$ represents OH; a group hydrolysable in vivo to OH or hydrogen; $C_{1-8}$ alkoxy; $C_{2-8}$ alkenyloxy; $C_{2-8}$ alkynyloxy; $C_{3-8}$ cycloalkyloxy; or $COR_{13}$ wherein $R_{13}$ represents hydrogen, $C_{1-8}$ alkyl, phenyl or phenyl $C_{1-4}$ alkyl; in which any phenyl moiety is optionally substituted by up to 3 substituents independently selected from $C_{1-6}$ alkoxy, $C_{1-6}$ alkyl, halo, $C_{1-6}$ alkoxycarbonyl, cyano, $C_{1-6}$ alkylthio or $C_{1-6}$ alkylsulphonyl; enhance acetylcholine function via an action at muscarinic receptors within the central nervous system and are therefore of potential use in the treatment and/or prophylaxis of dementia in mammals.

6 Claims, No Drawings

1,2,5,6-TETRAHYDROPYRIDINE OXIME DERIVATIVES

This invention relates to compounds having pharmaceutical activity, to a process for their preparation and their use as pharmaceuticals.

EP-0288394, U.S. Pat. Nos. 4,921,868 and 4,902,699 disclose certain 1,2,5,6-tetrahydropyridine 3-ketoxime and -3-aldoxime derivatives having cholinomimetic activity.

A novel group of compounds has now been discovered which enhance acetylcholine function via an action at muscarinic receptors within the central nervous system and are therefore of potential use in the treatment and/or prophylaxis of dementia in mammals.

According to the present invention, there is provided a compound of formula (I) or a pharmaceutically acceptable salt thereof:

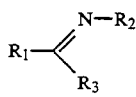
(I)

wherein $R_1$ represents a 1,2,5,6-tetrahydropyridin-3-yl group N-substituted by $R_{10}$ wherein $R_{10}$ represents OH; a group hydrolysable in vivo to OH or hydrogen; $C_{1-8}$ alkoxy; $C_{2-8}$ alkenyloxy; $C_{2-8}$ alkynyloxy; $C_{3-8}$ cycloalkyloxy; or $COR_{13}$ wherein $R_{13}$ represents hydrogen, $C_{1-8}$ alkyl, phenyl or phenyl $C_{1-4}$ alkyl; in which any phenyl moiety is optionally substituted by up to 3 substitutents independently selected from $C_{1-6}$ alkoxy, $C_{1-6}$ alkyl, halo, $C_{1-6}$ alkoxycarbonyl, cyano, $C_{1-6}$ alkylthio or $C_{1-6}$ alkylsulphonyl;

$R_2$ is a group $OR_4$, where $R_4$ is $C_{1-4}$ alkyl, $C_{2-4}$ alkenyl, $C_{2-4}$ alkynyl, a group $OCOR_5$ where $R_5$ is hydrogen or $R_4$, or a group $NHR_6$ or $NR_7R_8$ where $R_6$, $R_7$ and $R_8$ are independently $C_{1-2}$ alkyl; and $R_3$ is chloro, fluoro, bromo, $C_{1-3}$ alkyl substituted by one, two or three halogen atoms, or $R_3$ is a group $(CH_2)_n R_9$ where $R_9$ is —CN, —OH, —OCH$_3$, —SH or —SCH$_3$ and n is 0 or 1, with the proviso that when n is 0, $R_9$ is not —OH or —SH.

The term halogen includes bromine, chlorine, fluorine and iodine. $R_3$ halo is preferably fluorine. Halo in $R_{10}$ is preferably chlorine.

Compounds of formula (I) are capable of existing in a number of stereoisomeric forms including geometric isomers such as syn and anti and, for certain compounds, enantiomers. The invention extends to each of these stereoisomeric forms, and to mixtures thereof (including racemates). The different stereoisomeric forms may be separated one from the other by the usual methods, or any given isomer may be obtained by stereospecific or asymmetric synthesis.

The compounds of formula (I) can form acid addition salts with acids, such as the conventional pharmaceutically acceptable acids, for example hydrochloric, hydrobromic, phosphoric, acetic, fumaric, salicylic, citric, lactic, mandelic, tartaric, oxalic and methanesulphonic.

The term pharmaceutically acceptable salt encompasses solvates and hydrates. Thus where compounds of formula (I) or pharmaceutically acceptable salts thereof form solvates or hydrates, these also form an aspect of the invention.

Examples of suitable groups hydrolysable in vivo to OH include $C_{1-8}$ alkanoyloxy, $C_{1-8}$ alkoxycarbonyloxy, phenyl $C_{1-4}$ alkanoyloxy and —OCONHR$_{12}$ wherein $R_{12}$ is hydrogen, $C_{1-8}$ alkyl, $C_{2-8}$ alkenyl, $C_{2-8}$ alkynyl, $C_{3-8}$ cycloalkyl, phenyl or phenyl $C_{1-4}$ alkyl, in which any phenyl moiety is optionally substituted as aforesaid.

Examples of suitable groups hydrolysable in vivo to hydrogen include COOZ in which Z represents $C_{1-18}$ alkyl optionally substituted by tri $C_{1-6}$ alkylsilyl or $C_{1-6}$ alkylsulphonyl, $C_{2-18}$ alkenyl, $C_{2-18}$ alkynyl, $C_{3-8}$ cycloalkyl $C_{1-4}$ alkyl, $C_{3-10}$ cycloalkyl, phenyl or phenyl $C_{1-4}$ alkyl; in which any phenyl moiety is optionally substituted as aforesaid.

In a preferred aspect, therefore, $R_{10}$ represents COOZ in which Z represents $C_{1-18}$ alkyl optionally substituted by tri $C_{1-6}$ alkylsilyl or $C_{1-6}$ alkylsulphonyl, $C_{2-18}$ alkenyl, $C_{2-18}$ alkynyl, $C_{3-8}$ cycloalkyl $C_{1-4}$ alkyl, $C_{3-10}$ cycloalkyl, phenyl or phenyl $C_{1-4}$ alkyl; $OR_{11}$ wherein $R_{11}$ represents hydrogen, $C_{1-8}$ alkyl, $C_{2-8}$ alkenyl, $C_{2-8}$ alkynyl, $C_{3-8}$ cycloalkyl, $C_{1-8}$ alkanoyl, $C_{1-8}$ alkoxycarbonyl, phenyl $C_{1-4}$ alkanoyl or CONHR$_{12}$ wherein $R_{12}$ is hydrogen, $C_{1-8}$ alkyl, $C_{2-8}$ alkenyl, $C_{2-8}$ alkynyl, $C_{3-8}$ cycloalkyl, phenyl or phenyl $C_{1-4}$ alkyl; or $COR_{13}$ wherein $R_{13}$ represents hydrogen, $C_{1-8}$ alkyl, phenyl or phenyl $C_{1-4}$ alkyl; in which any phenyl moiety is optionally substituted as aforesaid.

Aliphatic Z in $R_{10}$ preferably contains up to 8 carbon atoms, more preferably up to 6.

Aliphatic $R_{11}$ and $R_{13}$ groups in $R_{10}$ preferably contain up to 4 carbon atoms. Phenylalkyl or phenylalkanoyl groups in $R_{10}$ are preferably phenyl-$C_{1-2}$ alkyl or -$C_{1-2}$ alkanoyl.

Substituents on phenyl in $R_{10}$ preferably contain up to 3 carbon atoms.

Examples of $R_{10}$ groups include COOZ in which Z is methyl, ethyl, n-propyl, iso-propyl, n-butyl, t-butyl, allyl, benzyl, phenethyl, phenyl, 4-chlorophenyl, 4-isopropylphenyl, 3,4-dimethoxyphenyl, adamantyl, 2-methylsulphonylethyl or 2-trimethylsilylethyl, and $OR_{11}$ where $R_{11}$ is hydrogen, methyl, ethyl, acetyl, pivaloyl, ethoxycarbonyl, benzoyl or CONHR$_{12}$ where $R_{12}$ is ethyl, n-propyl, iso-propyl, n-butyl, phenyl, 4-chlorophenyl, 4-isopropylphenyl, 4-methoxyphenyl, 3-chlorophenyl, 3-methoxyphenyl, 3,4-dichlorophenyl or 1-phenyl-1-ethyl.

Preferred examples of $R_{10}$ include hydroxy, phenyloxycarbonyl, 4-methoxyphenyloxycarbonyl, 3,4-dimethoxyphenyloxycarbonyl, acetoxy, propylaminocarbonyloxy and phenylaminocarbonyloxy.

The groups $R_4$ and $R_5$ in $R_2$ are preferably selected from methyl, ethyl, allyl and propargyl. $R_6$, $R_7$ and $R_8$ are preferably methyl. Suitable values for $R_2$ include methoxy, ethoxy, allyloxy, propargyloxy, acetoxy and dimethylamino, preferably methoxy.

Suitable examples for $R_3$ include methoxy, chloro, fluoro and bromo and when $R_3$ is a group $(CH_2)_n R_9$ and n is 0, an example of $R_9$ is —CN. When n is 1, an example of $R_9$ is CN.

The invention also provides a process for the preparation of a compound of formula (I), or a pharmaceutically acceptable salt thereof, which process comprises:

(a) reacting a compound of formula (II):

(II)

with a compound of formula (III):

$$R_2'\text{---}NH_2 \quad (III)$$

wherein $R_1'$ represents $R_1$ or a group convertible thereto, $R_2'$ represents $R_2$ or hydroxy, and $R_3'$ represents $R_3$ or a group convertible thereto, converting $R_2'$ to $R_2$ when hydroxy, converting $R_1'$ and $R_3'$ when other than $R_1$ and $R_3$ to $R_1$ and $R_3$, wherein $R_1$, $R_2$ and $R_3$ are as defined in formula (I), and thereafter optionally forming a pharmaceutically acceptable salt;

(b) reacting a compound of formula (IV):

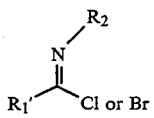
(IV)

with a compound of formula (V):

$$M\text{---}R_3' \quad (V)$$

capable of generating an $R_3'$ nucleophile wherein $R_1'$ represents $R_1$ or a group convertible thereto, $R_3'$ represents $R_3$ or a group convertible thereto, converting $R_1'$ and $R_3'$ when other than $R_1$ and $R_3$ to $R_1$ and $R_3$, wherein $R_1$, $R_2$ and $R_3$ are as defined in formula (I), and thereafter optionally forming a pharmaceutically acceptable salt;

(c) reacting a compound of formula (IVa):

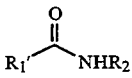
(IVa)

wherein $R_1'$ is $R_1$ or a group convertible thereto and wherein $R_1$ and $R_2$ are as defined in formula (I), with a chlorinating, brominating or fluorinating agent, converting $R_1'$ when other than $R_1$ to $R_1$, optionally converting $R_3$ when chloro or bromo to other $R_3$, wherein $R_3$ is as defined in formula (I) and thereafter optionally forming a pharmaceutically acceptable salt;

(d) the nitrosation of a compound of formula (IVb):

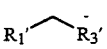
(IVb)

wherein $R_1'$ and $R_3'$ are as defined in formula (II), and thereafter converting the resulting $=$NOH group to $=$NR$_2$ wherein $R_2$ is as defined in formula (I), converting $R_1'$ and $R_3'$ when other than $R_1$ and $R_3$ to $R_1$ and $R_3$ and optionally forming a pharmaceutically acceptable salt; or (e) reacting a compound of formula (IVc)

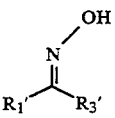
(IVc)

wherein $R_1'$ and $R_3'$ represent $R_1$ and $R_3$ as defined in formula (I) or groups convertible thereto, to convert the hydroxy group to $R_2$ as defined in formula (I), and thereafter converting $R_1'$ and $R_3'$ when other than $R_1$ and $R_3$ to $R_1$ and $R_3$ and optionally forming a pharmaceutically acceptable salt.

It will be appreciated that compounds of formula (IV) are identical to compounds of formula (I) in which $R_1'$ is $R_1$ and $R_3$ is chloro or bromo, and as such are themselves part of the invention.

The reaction between the compounds of formulae (II) and (III) is preferably carried out in a hydroxylic solvent such as methanol or ethanol, at ambient temperature, or where appropriate, in an inert solvent such as toluene at elevated temperature.

Where $R_2$ in compounds of formula (I) is a group $OR_4$, $NHR_6$ or $NR_7R_8$, a compound of formula (II) is conveniently reacted with a compound of formula (III) in which $R_2'$ is $R_2$.

Where $R_2$ in compounds of formula (I) is a group $OCOR_5$, a compound of formula (II) may be reacted with the compound of formula (III) in which $R_2'$ is hydroxy, with subsequent acylation of the resulting oxime of formula (IVc) by treatment with a suitable acylating agent such as an acyl halide, for example acetyl chloride.

The reaction between compounds of formulae (IV) and (V) may be carried out under standard conditions for the displacement of halogen by a nucleophile.

Where $R_3$ in compounds of formula (I) is fluoro, the residue M is suitably caesium, the caesium fluoride reagent being supported on calcium fluoride in dimethylformamide at elevated temperature for a prolonged period.

The nitrosation of a compound of formula (IVb) is preferably carried out using t-butyl nitrite and a base such as sodium ethoxide or, more preferably, potassium t-butoxide, and $R_3'$ is preferably an electron withdrawing group other than halo, such as CN. The resulting $=$NOH group in the oxime of formula (IVc) may be converted to $=$NR$_2$ by conventional routes such as acylation as described above or alkylation with an alkylating agent such as methyltosylate or an alkyl halide, for example methyl iodide. It will be appreciated that $R_3'$ is preferably other than halo, such as CN.

The product of the reaction of compounds of formulae (II) and (III) and formulae (IV) and (V) and the nitrosation of the compound of formula (IVb) is a compound of formula (IIa):

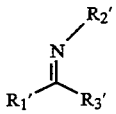
(IIa)

wherein $R_2'$ represents $R_2$ or hydroxy and $R_1'$ and $R_3'$ represent $R_1$ and $R_3$ or a groups convertible thereto, and $R_1$, $R_2$ and $R_3$ are as defined in formula (I).

It will be appreciated that the reaction of compounds of formula (IVa) with a chlorinating, brominating or fluorinating agent will yield compounds of formula (I) wherein $R_3$ is chloro, bromo or fluoro. Suitable chlorinating agents include phosphorus pentachloride which undergoes reaction in nitromethane at reduced temperature, for example 0° C., and dichlorontriphenylphosphine or carbon tetrachloride/triphenyl phosphine which undergoes reaction in acetonitrile at elevated temperature, for example at the boiling point of the solvent. Suitable brominating agents include dibromotriphenylphosphine or carbon tetrabromide/triphenylphosphine which undergoes reaction in acetonitrile at elevated temperature, for example at the boiling point of the solvent. Suitable fluorinating agents include diethylaminosulphur trifluoride (DAST) which also undergoes reaction in acetonitrile at elevated temperature.

Conversion of the resulting $R_3$ halogen group when chloro or bromo to other $R_3$ groups may be effected by reaction variant (b) above.

Examples of groups $R_1'$ convertible to $R_1$ include pyridin-3-yl, 1-oxopyridinium-3-yl and 1-alkyl-pyridinium-3-yl. A pyridin-3-yl group may be converted to a 1-substituted pyridinium-3-yl group by treatment with an alkylating agent such as a halide derivative e.g. methyl iodide and the pyridinium moiety converted to the required tetrahydropyridine moiety by reduction with a suitable reducing agent such as sodium borohydride. Dealkylation may be effected by treatment with a suitable chloroformate ester reagent. For example, demethylation may be effected with α-chloroethylchloroformate (R. A. Olofson et. al., J. Org. Chem. 1984 49 2081) in dichloromethane followed by methanol.

Certain intermediates of formula (IIa) wherein $R_1'$ is not $R_1$ when $R_2'$ is $R_2$ and $R_3'$ is $R_3$ and salts thereof, also form part of the invention, in particular compounds of formula (IIa) wherein $R_1'$ is 1-oxopyridinium-3-yl.

Introduction of $R_{10}$=COOZ groups may be effected by treatment of the NH compound with an appropriate chloroformate ester such as 4-methoxyphenyl chloroformate in dry solvent such as toluene in the presence of base such as triethylamine at ambient temperature.

Introduction of $R_{10}$=$COR_{13}$ groups may be effected by acylation of the NH compound with an appropriate acyl halide or anhydride.

Introduction of $R_{10}$=$OR_{11}$ groups is preferably effected via $R_{10}$=hydroxy. The unsubstituted tetrahydropyridine moiety may be treated with disodium hydrogen phosphate and benzoyl peroxide to give the N-benzoyloxy derivative which may then be treated with base such as an alkali metal alkoxide e.g. sodium methoxide to yield the N-hydroxy derivative.

Alternatively, a pyridin-3-yl group may be converted to the N-oxide by treatment with a suitable oxidising agent such as m-chloro perbenzoic acid and the resulting 1-oxopyridinium group reduced to the 1-hydroxytetrahydropyridine moiety by reduction with a suitable reducing agent such as sodium borohydride.

The $R_{10}$=hydroxy group may then be derivatised by standard methods, for example by introduction of $R_{11}$=acyl or alkoxycarbonyl using the appropriate halo derivative $R_{11}$-hal in an inert solvent such as tetrahydrofuran. $R_{11}$ groups $CONHR_{12}$ may be introduced by reaction of the $R_{10}$=hydroxy group with the appropriate isocyanate in toluene at ambient temperature. $R_{11}$=alkyl may be introduced by reaction of the $R_{10}$ hydroxy compound with sodium hydride followed by treatment with an alkylating agent such as an alkyl halide.

Compounds of formula (II) and compounds of formulae (IV) and (IVa) may be prepared from an intermediate compound of formula (VI):

(VI)

in which L is a leaving group such as chloro, bromo, $C_{1-4}$ alkoxy or N-methoxy-N-methylamino and $R_1'$ is as defined in formula (II). A compound of formula (VI) in which L is preferably chloro or bromo may be reacted with N,O-dimethylhydroxylamine and the resulting N-methoxy-N-methylcarboxamide derivative or a carboxy ester derivative reacted with a compound of formula (V), suitably an organolithium or Grignard reagent, to provide a compound of formula (II). For example the reaction product of acetonitrile and lithium diisopropylamide will yield a compound of formula (II) where $R_3$ is $CH_2CN$. It will be appreciated that the resulting compound of formula (II) will be in the form of the lithium enolate salt.

A compound of formula (VI) may alternatively be reacted with a compound of formula (III) wherein $R_2'$ is $OR_4$, in chloroform or acetonitrile or a mixture as solvent, in the presence of a base such as pyridine or triethylamine, and the resulting derivative of formula (IVa) treated with a chlorinating or brominating agent to provide a compound of formula (IV) in which $R_2'$ is $OR_4$.

Novel compounds of formulae (II), (IV), (IVa), (IVb) and (IVc) also form part of the invention.

Compounds of formula (VI) and certain compounds of formula (II) may be prepared by conventional routes for preparing carboxylic acid derivatives from commercially available starting materials.

Thus, for example, compounds of formula (II) where $R_1'$ is pyridyl and $R_3'$ is $C_{1-3}$ alkyl substituted as defined or $CH_2R_9$ may be prepared by treatment of 3-bromopyridine with n-butyllithium followed by reaction with the appropriate α-substituted N-methoxy-N-methylacetamide.

The acetamide reagent may be prepared by reacting N,O-dimethyl hydroxylamine with the corresponding α-substituted acetic acid or an appropriate reactive derivative thereof in the presence of base such as triethylamine or 2,6-dimethylpyridine.

The compound of formula (IVb) wherein $R_1'$ is pyridyl and $R_3'$ is cyano is commercially available.

Compounds of formula (III) are known compounds or may be prepared by analogous methods to those for preparing known compounds. Certain compounds of formula (III) are commercially available.

The different stereoisomeric forms of compounds of formula (I) may be separated one from the other by the usual methods, for example using chromatographic methods. Enantiomers may be separated using chiral resolving agents or chiral chromatography, or any given isomer may be obtained by stereospecific or asymmetric synthesis.

Pharmaceutically acceptable salts of the compounds of formula (I) may be formed conventionally by reaction with the appropriate acid such as described above under formula (I).

The compounds of the present invention enhance acetylcholine function via an action at muscarinic receptors within the central nervous system and are therefore of potential use in the treatment and/or prophylaxis of dementia.

The present invention also provides a pharmaceutical composition, which comprises a compound of formula (I) or pharmaceutically acceptable salt thereof, and a pharmaceutically acceptable carrier.

The compositions may be in the form of tablets, capsules, powders, granules, lozenges, suppositories, reconstitutable powders, or liquid preparations such as oral or sterile parenteral solutions or suspensions.

In order to obtain consistency of administration it is preferred that a composition of the invention is in the form of a unit dose.

Unit dose presentation forms for oral administration may be tablets and capsules and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulphate.

The solid oral compositions may be prepared by conventional methods of blending, filling, tabletting or the like. Repeated blending operations may be used to distribute the active agent throughout those compositions employing large quantities of fillers. Such operations are of course conventional in the art. The tablets may be coated according to methods well known in normal pharmaceutical practice, in particular with an enteric coating.

Oral liquid preparations may be in the form of, for example, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel, or hydrogenated edible fats; emulsifying agents, for example lecithin, sorbitan monooleate, or acacia; non-aqueous vehicles (which may include edible oils), for example almond oil, fractionated coconut oil, oily esters such as esters of glycerine propylene glycol or ethyl alcohol; preservatives, for example methyl or propyl p-hydroxybenzoate or sorbic acid; and if desired conventional flavouring or colouring agents.

For parenteral administration, fluid unit dosage forms are prepared utilizing the compound and a sterile vehicle, and, depending on the concentration used, can be either suspended or dissolved in the vehicle. In preparing solutions the compound can be dissolved in water for injection and filter sterilized before filling into a suitable vial or ampoule and sealing. Advantageously, adjuvants such as a local anaesthetic, a preservative and buffering agents can be dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The compositions may contain from 0.1% to 99% by weight, preferably from 10–60% by weight, of the active material, depending on the method of administration.

The invention also provides a method of treatment and/or prophylaxis of dementia in mammals including humans, which comprises administering to the sufferer an effective amount of a compound of formula (I) or a pharmaceutically acceptable salt thereof.

The dose of the compound used in the treatment of such disorders will vary in the usual way with the seriousness of the disorders, the weight of the sufferer, and the relative efficacy of the compound. However, as a general guide suitable unit doses may be 0.05 to 250 mg, for example 0.2 to 50 mg and such unit doses may be administered more than once a day, for example two or three times a day, so that the total daily dosage is in the range of about 0.01 to 50 mg/kg and such therapy may extend for a number of weeks or months.

When administered in accordance with the invention, no unacceptable toxicological effects are expected for the compounds of the invention.

In a further aspect the invention provides a compound of formula (I) or a pharmaceutically acceptable salt thereof for use as an active therapeutic substance.

The invention further provides a compound of formula (I) or a pharmaceutically acceptable salt thereof, for use in the treatment and/or prophylaxis of dementia.

In another aspect the invention provides the use of a compound of formula (I) or a pharmaceutically acceptable salt thereof for the preparation of a medicament for the treatment and/or prophylaxis of dementia.

The following examples illustrate the invention and the following descriptions illustrate the preparation of intermediates thereto.

DESCRIPTION 1

1-Methyl-1,2,5,6-tetrahydropyridin-3-yl-N-methoxycarboxamide (D1)

Methyl (1-methyl-1,2,5,6-tetrahydropyridin-3-yl) carboxylate (1 g, 6.45 mmol) and potassium hydroxide (0.83 g, 14.82 mmol) in ethanol (25 ml) were heated at reflux for 9 h. The reaction mixture was concentrated in vacuo and the residue treated carefully with hydrogen chloride in methanol until the solution was acidic. The solution was concentrated and dried under vacuum to give the carboxylic acid hydrochloride salt. Thionyl chloride (10 ml) was added and the mixture was heated at reflux under nitrogen for 1 h. The resulting solution was concentrated in vacuo to a gum which was freed from excess thionyl chloride by co-evaporation with toluene. The residue was dissolved in a mixture of chloroform (15 ml) and dry acetonitrile (15 ml), and methoxylamine hydrochloride (0.59 g, 7.07 mmol) was added. After cooling to $-20°$ C., pyridine (2.6 ml) was added dropwise over 0.5 h and the reaction mixture was allowed to warm to room temperature overnight. The solvent and excess pyridine were removed in vacuo and the residue was partitioned between saturated potassium carbonate solution (50 ml) and chloroform. The aqueous layer was further extracted with chloroform ($5 \times 50$ ml) and the combined organic extracts were dried ($Na_2SO_4$) and evaporated to a gum, which was chromatographed on silica using a graded eluant of 2–15% methanol/chloroform to afford the title compound (D1) (0.5 g, 38%) as an off-white solid.

$^1$H NMR (CDCl$_3$) δ: 2.30 (2H, m), 2.40 (3H, s), 2.53 (2H, t, J=6 Hz), 3.14 (2H, m), 3.27 (3H, s), 6.45 (1H, m)

DESCRIPTION 2

1-Methyl-1,2,5,6-tetrahydropyridin-3-yl-N-methoxycarboximidoyl fluoride (D2)

1-Methyl-1,2,5,6-tetrahydropyridin-3-yl-N-methoxycarboxamide (D1, 0.5 g, 2.94 mmol) was converted to the hydrofluoride salt by the addition of hydrogen fluoride-pyridine (Aldrich). The salt was dissolved in refluxing acetonitrile (50 ml) and diethylaminosulphur trifluoride (DAST) (0.41 ml, 3.10 mmol) in acetonitrile (5 ml) was added in a single portion. The reaction mixture was immediately cooled and poured into saturated potassium carbonate (50 ml) and extracted with chloroform (4×50 ml). The combined organic extracts were dried (Na₂SO₄) and evaporated to an oil which was chromatographed on silica using 0-1% methanol/chloroform as eluant to yield the title compound (D2) as an oil (0.24 g, 47%). Addition of oxalic acid and recrystallisation from methanol/acetone afforded a colourless crystalline solid m.p. 162°-164° C. (decomp.). Oxalate salt: $^1$H NMR (d$_6$ DMSO) δ: 2.54 (2H, m), 2.80 (3H, s), 3.20 (2H, m), 3.74 (2H, m), 3.82 (3H, s), 6.64 (1H, m). $^{13}$C NMR (d$_6$ DMSO) δ: 22.81, 42.23, 48.67, 48.83, 63.32, 119.38 (d, $^2J_{CF}$=26 Hz), 130.40, 147.87 (d, $^1J_{CF}$=322 Hz). MS: Calculated mass for C$_8$H$_{13}$N$_2$OF=172.1012 Observed mass=172.1012

DESCRIPTION 3

1,2,5,6-Tetrahydropyridin-3-yl-N-methoxycarboximidoyl fluoride (D3)

An ice cold solution of 1-methyl-1,2,5,6-tetrahydropyridin-3-yl-N-methoxycarboximidoyl fluoride (D2) (185 mg, 1.1 mmol) in dry dichloromethane (2 ml) was treated dropwise with α-chloroethyl chloroformate (160 mg, 1.13 mmol) under an atmosphere of nitrogen. After stirring at room temperature for 4 h, the reaction mixture was concentrated in vacuo. The residue was dissolved in dry methanol (4 ml) and heated under reflux for 1 h. The solution was concentrated in vacuo, treated with saturated aqueous potassium carbonate (5 ml) and extracted into chloroform (3×7 ml). The combined organic extracts were dried (Na₂SO₄) and concentrated in vacuo. The resulting gum was chromatographed on silica in a gradient of 0-3% methanol in chloroform to give the title compound (D3) as an oil (36 mg, 21%).

DESCRIPTION 4

α-(Methoxyimino)-α-pyridin-3-yl)acetonitrile (D4)

Method A

Sodium metal (0.19 g, 0.0083 mol) was dissolved in dry ethanol (15 ml) at room temperature with stirring. 3-Pyridylacetonitrile (1.0 g, 0.0083 mol) was added and stirred for 1 h. tert-Butyl nitrite (1.0 ml, 0.0085 mol) was added and the mixture stirred for a further 1 h after which time a yellow precipitate had formed. Methyl iodide (1.0 ml, 0.016 mol) was added and the mixture stirred at room temperature for 2 h. Aqueous potassium carbonate (10% solution, 50 ml) was added and the mixture extracted with chloroform (3×100 ml). The organic layers were separated and dried (Na₂SO₄) then filtered and evaporated to dryness. The residue was subjected to column chromatography on silica gel eluting with chloroform. The title compound (D4) was obtained as a colourless oil which crystallised on standing (0.155 g, 11%).

$^1$H NMR (CDCl₃) δ: 4.25 (3H, s), 7.39-7.45 (1H, m), 8.05-8.12 (1H, m), 8.61-8.75 (1H, m), 9.04 (1H, d).

Method B

To a solution of 3-pyridylacetonitrile (15 g, 0.127 mol) in dry tetrahydrofuran (900 ml) at −20° C. under a nitrogen atmosphere was added potassium-t-butoxide (17.2 g, 0.14 mol) portionwise over 5 min. Stirring was continued at this temperature for 1 h. t-Butylnitrite (16.6 ml, 0.14 mol) was then added and the mixture allowed to warm to room temperature. The mixture was stirred for a further 2 h then methyl iodide (10.5 ml, 0.168 mol) was added. The mixture was stirred for a further 20 h and then concentrated in vacuo. The residue was partitioned between 10% aqueous potassium carbonate solution and ethyl acetate. The organics were separated and dried (Na₂SO₄) and evaporated to dryness. The residue was subjected to column chromatography on silica gel eluting with 0-1% methanol/chloroform. This gave the title compound (D4) as an oil (17.6 g, 86%).

DESCRIPTION 5

α-(Methoxyimino)-α-(1-oxopyridinium-3-yl)acetonitrile (D5)

α-(Methoxyimino)-α-(1-pyridin-3-yl)acetonitrile (D4) (0.72 g, 0.0045 mol) was dissolved in dry dichloromethane (50 ml) and cooled to 0° C. m-Chloroperoxybenzoic acid (85% purity) (1.0 g, 0.0049 mol) was added with stirring. After 2 h a further amount of m-chloroperoxybenzoic acid (0.5 g, 0.0025 mol) was added and the mixture stirred for another 2 h. Aqueous potassium carbonate (10% solution, 100 ml) was added and the mixture extracted with chloroform (2×100 ml). The combined organic extracts were dried (Na₂SO₄), filtered and evaporated to dryness to give the title compound (D5) as a yellow crystalline solid (0.69 g, 87%).

$^1$H NMR (CDCl₃) δ: 4.27 (3H, s), 7.38 (1H, t, J=6 Hz), 7.62 (1H, d, J=8 Hz), 8.29 (1H, d, J=6 Hz), 8.67 (1H, s).

DESCRIPTION 6

α-(Methoxyimino)-α-(1-methylpyridinium-3-yl)acetonitrile iodide (D6)

α-(Methoxyimino)-α-(pyridin-3-yl)acetonitrile (D4) (0.155 g, 0.00096 mol) was heated under reflux with methyl iodide (5 ml) in methanol (5 ml) for 60 h. The mixture was evaporated to dryness to give the title compound (D6) (0.3 g, 100%) which was used without further purification.

DESCRIPTION 7

α-(Methoxyimino)-α-(1-methyl-1,2,5,6-tetrahydropyridin-3-yl)acetonitrile (D7)

α-(Methoxyimino)-α-(1-methylpyridinium-3-yl)acetonitrile iodide (D6) (0.3 g, 0.001 mol) was dissolved in methanol (10 ml) and cooled to 0° C. Sodium borohydride (0.114 g, 0.003 mol) was added in three equal portions at 15 minute intervals. The mixture was allowed to warm to room temperature over 1 h and then evaporated to dryness. The residue was partitioned between saturated aqueous potassium carbonate solution (50 ml) and chloroform (3×75 ml). The organic layers were separated and dried (Na₂SO₄) then filtered and evaporated to dryness. The residue was subjected to column chromatography on silica gel eluting with 0-1% methanol/chloroform. This gave the title compound (D7) as an oil (0.04 g, 23%). A portion of this material was converted to the oxalate salt and crystallised from ethanol/diethyl ether to give a white crystalline solid m.p. 157°-158° C.

Free base $^1$H NMR (CDCl₃) δ: 2.40 (3H, s), 2.40-2.49 (2H, m), 2.53-2.61 (2H, m), 3.13-3.20 (2H, m), 4.07 (3H, s), 6.50-6.55 (1H, m). MS Calculated for C₉H₁₃N₃O=179.1058 Observed mass=179.1057 Analysis (oxalate) $C_{11}H_{15}N_3O_5$ requires C:49.07; H:5.62; N:15.61; found C:49.17; H:5.72; N:15.59.

DESCRIPTION 8

α-(Methoxyimino)-α-(1,2,5,6-tetrahydropyridin-3-yl)acetonitrile (D8)

α-(Methoxyimino)-α-(1-methyl-1,2,5,6-tetrahydropyridin-3-yl)acetonitrile (D7) (0. 047 g, 0.00026 moles) was dissolved in dry dichloromethane (1 ml) and cooled to 0° C. under a nitrogen atmosphere. α-Chloroethyl chloroformate (0.041 g, 0.00029 moles) was added with stirring and the mixture allowed to warm to room temperature. The mixture was stirred for a further 4 h and then evaporated to dryness. Methanol (5 ml) was added and the mixture was heated under reflux for 1 h. Evaporation of the solvent gave an oil which was partitioned between saturated aqueous potassium carbonate and chloroform. The organic phase was separated and dried ($Na_2SO_4$) then evaporated to dryness. Column chromatography on silica-gel eluting with 0–2% methanol/chloroform gave the title compound (D8) as a crystallising oil (0.03 g, 69%). Treatment with anhydrous oxalic acid afforded a white crystalline solid m.p. 180°–190° C.

Oxalate salt: $^1$H NMR ($d_6$-DMSO) δ: 2.45–2.57 (2H, m), 3.12–3.21 (2H, m), 3.76 (2H, s), 4.08 (3H, s), 6.58–6.63 (1H, m), 7.00–8.30 (2H, br s). Analysis $C_8H_{11}N_3O.C_2H_2O_4$ requires C: 47.06; H: 5.13; N: 16.46; found C: 46.95; H: 5.14; N: 16.25.

DESCRIPTION 9

1-Methyl-1,2,5,6-tetrahydropyridin-3-yl)-N-methoxycarboximidoyl chloride (D9)

Triphenylphosphine (3.24 g, 12.37 mmol) was added in a single portion to 1-methyl-1,2,5,6-tetrahydropyridin-3-yl-N-methoxycarboxamide (D1, 2 g, 11.76 mmol) in acetonitrile (200 ml) and carbon tetrachloride (5 ml) at reflux. The mixture was heated under reflux for 0.5 h, cooled, then poured into saturated aqueous potassium carbonate solution (100 ml) and extracted with chloroform (4×100 ml). The combined extracts were washed with 1M hydrochloric acid (2×100 ml). The combined acid extracts were then basified and saturated with potassium carbonate and extracted with chloroform (4×150 ml). The organic extracts were dried ($Na_2SO_4$) and evaporated to an oil which was chromatographed on silica using ether as eluant to give the title compound (D9) as an oil (1.03 g, 46%). A portion of this material was converted to the oxalate salt and recrystallised from methanol/acetone to give a colourless solid m.p. 166° C. (decomp.).

Oxalate: $^1$H NMR ($d_6$ DMSO) δ: 2.56 (2H, m), 2.78 (3H, s), 3.16 (2H, t, J=6 Hz), 3.82 (2H, m), 3.98 (3H, s), 6.73 (1H, m). $^{13}$C NMR ($d_6$-DMSO) δ: 23.33, 42.59, 49.06, 51.10, 62.82, 125.93, 134.94, 163.11. Analysis: $C_8H_{13}N_2OCl.C_2H_2O_4$ requires C: 43.1; H: 5.43; N: 10.05; found C: 43.06; H: 5.39; N: 9.98.

DESCRIPTION 10

1,2,5,6-Tetrahydropyridin-3-yl-N-methoxycarboximidoyl chloride (D10)

1-Methyl-1,2,5,6-tetrahydropyridin-3-yl-N-methoxycarboximidoyl chloride (D9) (2.0 g, 0.01 moles) was treated with α-chloroethyl chloroformate as in the method of Description 3. This gave the title compound (D10) as a crystallising oil (0.99 g, 53%). A small amount was treated with anhydrous oxalic acid and the resulting oxalate salt was recrystallised from ethanol/diethyl ether to give a white crystalline solid m.p. 183°–5° C.

Oxalate: $^1$H NMR ($d_6$-DMSO) δ: 2.52–2.65 (2H, m), 3.25–3.31 (2H, m), 3.86–3.94 (2H, m), 4.07 (3H, s), 3.40–4.50 (3H, br s), 6.83 (1H, m). Analysis $C_7H_{11}N_2OCl.C_2H_2O_4$ requires C:40.83; H:4.91; N:10.59; found C:40.62; H:4.90; N:10.35.

EXAMPLE 1

1,2,5,6-Tetrahydro-1-(4-methoxyphenyloxycarbonyl)-pyridin-3-yl-N-methoxycarboximidoyl fluoride (E1)

An ice cold solution of 1,2,5,6-tetrahydropyridin-3-yl-N-methoxycarboximidoyl fluoride (D3) (50 mg, 0.32 mmol) in dry toluene (5 ml) containing dry triethylamine (35 mg, 0.35mmol) was treated dropwise with 4-methoxyphenyl chloroformate (65 mg, 0.35 mmol), under an atmosphere of nitrogen. After stirring at room temperature for 40 min the solution was diluted with chloroform (50 ml) and washed with dilute hydrochloric acid (50 ml), dried ($Na_2SO_4$) then concentrated in vacuo. The residue was chromatographed on neutral alumina in a gradient of 5–10% ethyl acetate in cyclohexane to give a solid which was recrystallised from hexane to afford the title compound (E1) as a white solid (70 mg, 72%) m.p. 91°–93° C.

$^1$H NMR ($d_6$-DMSO, 80° C.) δ: 2.39–2.44 (2H, m), 3.60–3.68 (2H, m), 3.78 (3H, s), 3.85 (3H, s), 4.13–4.18 (2H, m), 6.62–6.66 (1H, m), 6.91–6.96 (2H, m), 7.05–7.10 (2H, m) Analysis $C_{15}H_{17}FN_2O_4$ requires C: 58.44; H: 5.56; N: 9.09; found C: 58.49; H: 5.56; N: 9.24.

EXAMPLE 2

α-(Methoxyimino)-α-(1-hydroxy-1,2,5,6-tetrahydropyridin-3-yl)acetonitrile (E2)

Sodium borohydride (0.13 g, 0.0034 mol) was added to a mixture of methanol (5 ml) and water (5 ml) at 0° C. To this was added dropwise a solution of α-(methoxyimino)-α-(1-oxopyridinium-3-yl)acetonitrile (D5) (0.2 g, 0.0011 mol) in methanol (30 ml) and water (5 ml). The mixture was allowed to warm to room temperature and stirred for a further 2 h. The mixture was evaporated to dryness and the residue partitioned between saturated aqueous potassium carbonate (25 ml) and chloroform(3×30 ml). The organic extracts were combined and dried ($Na_2SO_4$) then filtered and evaporated to dryness. The residue was subjected to column chromatography on silica gel eluting with 0–2% methanol/chloroform to give a solid which was recrystallised from ethyl acetate/pentane to afford the title compound (E2) as a white crystalline solid (0.135 g, 67%) m.p. 145°–147° C.

$^1$H NMR ($CDCl_3$) δ: 2.42–2.59 (2H, m), 2.90–3.03 (1H, m), 3.10–3.26 (1H, m), 3.35–3.52 (1H, m), 3.83–3.95 (1H, m), 4.08 (3H, s), 6.47–6.51 (1H, m). Analysis $C_8H_{11}N_3O_2$ requires C: 53.03; H: 6.12; N: 23.19; found: C: 53.27; H: 6.19; N: 23.10.

EXAMPLE 3

α-(Methoxyimino)-α-[1,2,5,6-tetrahydro-1-(phenyloxycarbonyl)pyridin-3-yl]acetonitrile (E3)

α-(Methoxyimino)-α-(1,2,5,6-tetrahydropyridin-3-yl)acetonitrile (D8) (0.5 g, 0.003 moles) was treated with phenyl chloroformate (0.42 ml, 0.0033 moles) according to the method of Example 1. The crude product was crystallised from diethyl ether/pentane to give the title compound (E3) as a white crystalline solid (0.7 g, 81%) m.p. 111°-112° C.

$^1$H NMR (CDCl$_3$) δ: 2.42–2.58 (2H, br s), 3.63–3.80 (2H, m), 4.10 (3H, s), 4.27–4.41 (2H, m), 6.60–6.73 (1H, br s), 7.05–7.41 (5H, m). Analysis C$_{15}$H$_{15}$N$_3$O$_3$ requires C: 63.15; H: 5.30; N: 14.73; found C: 63.31; H: 5.30; N: 14.70.

EXAMPLE 4

α-(Methoxyimino)-α-[1,2,5,6-tetrahydro-1-(4-methoxyphenyloxycarbonyl)pyridin-3-yl]acetonitrile (E4)

α-(Methoxyimino)-α-(1,2,5,6-tetrahydropyridin-3-yl)acetonitrile (D8) (0.5 g, 0.003 moles) was treated with 4-methoxyphenylchloroformate (0.5 ml, 0.0033 moles) as in the method of Example 1. The crude produce was triturated with pentane to give the title compound (E4) as a white crystalline solid (0.81 g, 85%) m.p. 75°-76° C.

$^1$H NMR (CDCl$_3$) δ: 2.42–2.53 (2H, br s), 3.14–3.79 (2H, m), 3.80 (3H, s), 4.10 (3H, s), 4.25–4.39 (2H, m), 6.60–6.71 (1H, br s), 6.87 (2H, d, J=11 Hz), 7.03 (2H, d, J=11 Hz) Analysis C$_{16}$H$_{17}$N$_3$O$_4$ requires C: 60.94; H: 5.43; N: 13.33; found C: 60.94; H: 5.35; N: 13.10.

EXAMPLE 5

α-(Methoxyimino)-α-[1,2,5,6-tetrahydro-1-(3,4-dimethoxyphenyloxycarbonyl)pyridin-3-yl]acetonitrile (E5)

α-(Methoxyimino)-α-[1,2,5,6-tetrahydropyridin-3-yl]acetonitrile (D8) (0.5 g, 0.003 moles) was treated with 3,4-dimethoxyphenylchloroformate* (0.67 g, 0.0031 moles) as in the method of Example 1. The crude product was crystallised from diethyl ether/hexane to give the title compound (E5) as a white crystalline solid (0.65 g, 62%) m.p. 99°-100° C.

$^1$H NMR (CDCl$_3$) δ: 2.45–2.55 (2H, br s), 3.65–3.80 (2H, m), 3.85 (6H, s), 4.10 (3H, s), 4.27–4.41 (2H, m), 6.61–6.72 (3H, m), 6.84 (1 h, d, J=12 Hz). Analysis C$_{17}$H$_{19}$N$_3$O$_5$ requires C: 59.12; H: 5.55; N: 12.17; found C: 59.33; H: 5.58; N: 12.07.

*3,4-Dimethoxyphenylchloroformate was prepared by treating an aqueous solution of the sodium salt of 3,4-dimethoxyphenol with 12.5% phosgene in toluene solution in the presence of Adogen 464 (Aldrich) phase transfer catalyst according to the general method of W. Moszczynski et al, Przem. Chem., 1971, 50(3), 176 (CA 74:141351e).

EXAMPLE 6

1-Hydroxy-1,2,5,6-tetrahydropyridin-3-yl-N-methoxycarboximidoyl chloride hydrochloride salt (E6)

1,2,5,6-Tetrahydropyridin-3-yl-N-methoxycarboximidoyl chloride (D10) (0.5 g, 0.0028 moles) was dissolved in tetrahydrofuran (50 ml) and treated with disodium hydrogen phosphate (2.03 g, 0.014 moles) followed by benzoyl peroxide (1.1 g, 70% pure; 0.0031 moles) with stirring. The mixture was kept at ambient temperature for 60 hrs and then filtered. The filtrate was evaporated to dryness and the residue partitioned between saturated sodium bicarbonate solution and ethyl acetate. The organic layer was collected and dried (Na$_2$SO$_4$), filtered and evaporated to dryness. The residue was purified by flash chromatography on TLC silica gel eluting with 5% ethyl acetate in 60–80 petrol. This gave the N-benzoyloxy compound (0.26 g) which was dissolved in dry diethyl ether (10 ml) and methanol (2 ml) and treated with sodium methoxide (3.48 molar solution in methanol; 0.29 ml, 0.001 moles). The mixture was stirred at ambient temperature for 30 mins. Water (10 ml) was added and the resulting mixture extracted with diethyl ether (2×50 ml). The organics were separated, dried (Na$_2$SO$_4$), filtered and evaporated to dryness. The residue was dissolved in ethanol (1 ml) and treated with 1M hydrogen chloride in diethyl ether to give a crystalline solid. Recrystallisation from acetone/diethyl ether gave the title compound (E6) as a white crystalline solid (0.05 g, 9%) m.p. 135°–7° C.

$^1$H NMR (d$_6$-dMSO) δ: 2.56–2.72 (2H, m), 3.30–3.60 (2H, m), 3.95 (1H, d, J=20 Hz), 3.99 (3H, s), 4.25 (1H, d, J=20 Hz), 6.68–6.75 (1H, m), 11.63 (1H, br s). Analysis C$_7$H$_{11}$ClN$_2$O$_2$.HCl requires C: 37.02; H:5.33; N:12.34; found C:36.83; H:5.32; N:11.96.

EXAMPLE 7

1,2,5,6-Tetrahydro-1-(4-methoxyphenyloxycarbonyl)-pyridin-3-yl-N-methoxycarboximidoyl chloride (E7)

1,2,5,6-Tetrahydropyridin-3-yl-N-methoxycarboximidoyl chloride (D10) (0.106 g, 0.0006 moles) was treated with 4-methoxyphenylchloroformate as in the method of Example 1. The residue obtained was chromatographed on silica-gel eluting with 0–1% methanol in chloroform to give a gum which crystallised from ethyl acetate/pentane to give the title compound (E7) (0.11 g, 56%) m.p. 103°–5° C.

$^1$H NMR (CDCl$_3$) δ: 2.35–2.48 (2H, m), 3.61–3.78 (2H, m), 3.80 (3H, s), 4.02 (3H, s), 4.30–4.47 (2H, m), 6.65–6.67 (1H, m), 6.85 (2H, d, J=10 Hz), 7.02 (2H, d, J=10 Hz). Analysis C$_{15}$H$_{17}$ClN$_2$O$_4$ requires C:55.48; H:5.28; N:8.63; found C:55.38; H:5.29; N:8.55.

EXAMPLE 8

α-(Methoxyimino)-α-(1-propylaminocarbonyloxy-1,2,5,6-tetrahydropyridin-3-yl)acetonitrile (E8)

Propyl isocyanate (0.23 g, 0.00275 moles) was added to a solution of α-(methoxyimino)-α-(1-hydroxy-1,2,5,6-tetrahydropyridin-3-yl)acetonitrile (E2) (0.45 g, 0.0025 moles) in dry toluene (20 ml) with stirring. The mixture was kept at ambient temperature for 2 hrs then evaporated to dryness. The resulting residue crystallised from ethyl acetate/60–80 petrol. Recrystallisation from the same solvent system gave the title compound (E8) as a white crystalline solid (0.37 g, 56%) m.p. 95°–6° C.

$^1$H NMR (CDCl$_3$) δ: 0.95 (3H, t, J=7 Hz), 1.49–1.63 (2H, m), 2.45–2.68 (2H, m), 3.17–3.27 (4H, m), 3.68–3.75 (1H, brs), 3.85–3.95 (1H, brs), 4.10 (3H, s), 6.50–6.60 (2H, m). Analysis C$_{12}$H$_{18}$N$_4$O$_3$ requires C:54.12; H:6.81; N:21.04; found C:54.03; H:6.75; N:20.99.

EXAMPLE 9

α-(Methoxyimino)-α-(1-phenylaminocarbonyloxy-1,2,5,6-tetrahydropyridin-3-yl)acetonitrile (E9)

α-(Methoxyimino)-α-(1-hydroxy-1,2,5,6-tetrahydropyridin-3-yl)acetonitrile (E2) (0.45 g, 0.0025 moles) was treated with phenyl isocyanate as in the method of Example 8. The residue obtained was chromatographed on silica gel eluting with 0–1% methanol/chloroform to give a crystalline solid. Recrystallisation from ethyl acetate/60–80 petrol gave the title compound (E9) as white crystals (0.245 g, 33%) m.p. 128°–130° C.

$^1$H NMR (CDCl$_3$) δ: 2.45–2.75 (2H, m), 3.27–3.37 (2H, m), 3.75–4.03 (2H, m), 4.08 (3H, s), 6.58–6.63 (1H, m), 7.12 (1H, t, J=7 Hz ), 7.32 (2H, t, J=7 Hz), 7.47 (2H, d, J=10 Hz), 8.45–8.52 (1H, br s). Analysis C$_{15}$H$_{16}$N$_4$O$_3$ requires C:59.99; H:5,37; N:18.66; found C:60.10; H:5.42; N:18.69.

EXAMPLE 10

α-(Methoxyimino)-α-(1-acetoxy-1,2,5,6-tetrahydropyridin-3-yl)acetonitrile (E10)

α-(Methoxyimino)-α-(1-hydroxy-1,2,5,6-tetrahydropyridin-3-yl)acetonitrile (E2) (0.5 g, 0.0028 moles) was dissolved in dry tetrahydrofuran (20 ml) and treated with triethylamine (0.43 ml, 0.0031 moles) with stirring at room temperature. This mixture was then treated with acetyl chloride (0.22 ml, 0.0031 moles) and stirred at ambient temperature for 2 h. The mixture was filtered and the filtrate evaporated to dryness. The residue was chromatographed on silica gel eluting with chloroform. The crystalline residue was recrystallised from 60–80 petrol to give the title compound (E10) as an off-white crystalline solid (0.234 g, 38%) m.p. 87°–8° C.

$^1$H NMR (CDCl$_3$) δ: 2.07 (3H, s), 2.49–2.60 (2H, m), 3.19–3.28 (2H, m), 3.60–4.05 (2H, br s), 4.07 (3H, s), 6.52–6.59 (1H, m). Analysis C$_{10}$H$_{13}$N$_3$O$_3$ requires C:53.81; H:5.87; N:18.82; found C:54.02; H:5.91; N:18.82.

| Compound | R$_{10}$ | R$_2$ | R$_3$ |
|---|---|---|---|
| E1 | 4-Methoxyphenyloxycarbonyl | OCH$_3$ | F |
| E2 | OH | OCH$_3$ | CN |
| E3 | Phenyloxycarbonyl | OCH$_3$ | CN |
| E4 | 4-Methoxyphenyloxycarbonyl | OCH$_3$ | CN |
| E5 | 3,4-Dimethoxyphenyloxycarbonyl | OCH$_3$ | CN |
| E6 | OH | OCH$_3$ | Cl |
| E7 | 4-Methoxyphenyloxycarbonyl | OCH$_3$ | Cl |
| E8 | Propylaminocarbonyloxy | OCH$_3$ | CN |
| E9 | Phenylaminocarbonyloxy | OCH$_3$ | CN |
| E10 | Acetoxy | OCH$_3$ | CN |

Biological Activity

Determination of central muscarinic activity

Male mice (CD1, Charles River) weighing 25–35 g are used. Body temperature is measured using an electronic thermometer with a rectal probe.

At 30 minutes predose, atropine methyl nitrate (0.3 mgkg$^{-1}$ sc) is administered in order to block peripheral effects of the compound under study. Test compound is administered subcutaneously at time (t)=O and body temperature is recorded at t=O, 15, 30, 45, 60, 90 and 120 minutes post dose. The dose which induces a 3° C. drop in body temperature compared to control is noted. Duration of action of the test compound is calculated as the time taken for the hypothermic response of 3° C. to be reduced by half (i.e. to 1.5° C).

| Compound | Effective dose (−3° C.) mg/kg | Duration min |
|---|---|---|
| 2 | 2.0 | 90 |
| 4 | 0.9 | 180 |
| 5 | 0.6 | 180 |

We claim:

1. A compound of Formula (I) or a pharmaceutically acceptable salt thereof:

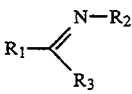

wherein R$_1$ represents a 1,2,5,6-tetrahydropyridin-3-yl group N-substituted by R$_{10}$ wherein R$_{10}$ represents OH; C$_{1-8}$ alkanoyloxy, C$_{1-8}$ alkoxycarbonyloxy, phenyl C$_{1-4}$ alkanoyloxy and —OCONHR$_{12}$ wherein R$_{12}$ is hydrogen, C$_{1-8}$ alkyl, C$_{2-8}$ alkenyl, C$_{2-8}$ alkynyl, C$_{3-8}$ cycloalkyl, phenyl or phenyl C$_{1-4}$ alkyl, or R$_{10}$ is COOZ in which Z represents C$_{1-18}$ alkyl optionally substituted by tri C$_{1-6}$ alkylsilyl or C$_{1-6}$ alkylsulphonyl, C$_{2-18}$ alkenyl, C$_{2-18}$ alkynyl, C$_{3-8}$ cycloalkyl C$_{1-4}$ alkyl, C$_{3-10}$ cycloalkyl, phenyl or phenyl C$_{1-4}$ alkyl; C$_{1-8}$ alkoxy; C$_{2-8}$ alkenyloxy; C$_{2-8}$ alkynyloxy; C$_{3-8}$ cycloalkyloxy; or COR$_{13}$ wherein R$_{13}$ represents hydrogen, C$_{1-8}$ alkyl, phenyl or phenyl C$_{1-4}$ alkyl; any of the above phenyl moieties is optionally substituted by up to 3 substituents independently selected from C$_{1-6}$ alkoxy, C$_{1-6}$ alkyl, halo, C$_{1-6}$ alkoxycarbonyl, cyano, C$_{1-6}$ alkylthio or C$_{1-6}$ alkylsulphonyl; R$_2$ is a group OR$_4$ where R$_4$ is C$_{1-4}$ alkyl, C$_{2-4}$ alkenyl, C$_{2-4}$ alkynyl, a group OCOR$_5$ where R$_5$ is hydrogen or R$_4$, or a group NHR$_6$ or NR$_7$R$_8$ where R$_6$, R$_7$ and R$_8$ are independently C$_{1-2}$ alkyl; and R$_3$ is chloro, fluoro, bromo, C$_{1-3}$ alkyl substituted by one, two or three halogen atoms, or R$_3$ is a group (CH$_2$)$_n$R$_9$ where R$_9$ is —CN, —OH, —OCH$_3$, —SH or SCH$_3$ and n is O or 1, with the provisio that when n is O, R$_9$ is not —OH or —SH.

2. A compound according to claim 1 wherein R$_{10}$ is selected from hydroxy, phenyloxycarbonyl, 4-methoxyphenyloxycarbonyl, 3,4-dimethoxyphenyloxycarbonyl, acetoxy, propylaminocarbonyloxy and phenylaminocarbonyloxy.

3. A compound according to claim 1 wherein R$_4$ and R$_5$ in R$_2$ are selected from methyl, ethyl, allyl and propargyl and R$_6$, R$_7$ and R$_8$ in R$_2$ are methyl.

4. A compound according to claim 1 where R$_3$ is selected from methoxy, chloro, fluoro, bromo, CN and CH$_2$CN.

5. A compound according to claim 1 selected from the group consisting of:
1,2,5,6-tetrahydro-1-(4-methoxyphenyloxycarbonyl)-pyridin-3-yl-N-methoxycarboximidoyl fluoride;
α-(methoxyimino)-α-(1-hydroxy-1,2,5,6-tetrahydropyridin-3-yl)acetonitrile;
α-(methoxyimino)-α-[1,2,5,6-tetrahydro-1-(phenyloxy-carbonyl)pyridin-3-yl]acetonitrile;
α-(methoxyimino)-α-[1,2,5,6-tetrahydro-1-(4-methoxy-phenyloxycarbonyl)pyridin-3-yl]acetonitrile;
α-(methoxyimino)-α-[1,2,5,6-tetrahydro-1-(3,4-dimethoxyphenyloxycarbonyl)pyridin-3-yl]acetonitrile;
1-hydroxy-1,2,5,6-tetrahydropyridin-3-yl-N-methoxycarboximidoyl chloride;
1,2,5,6-tetrahydro-1-(4-methoxyphenyloxycarbonyl)-pyridin-3-yl-N-methoxycarboximidoyl chloride;
α-(methoxyimino)-α-(1-propylaminocarbonyloxy-1,2,5,6-tetrahydropyridin-3-yl)acetonitrile;
α-(methoxyimino)-α-(1-phenylaminocarbonyloxy-1,2,5,6-tetrahydropyridin-3-yl)acetonitrile; and
α-(methoxyimino)-α-(1-acetoxy-1,2,5,6-tetrahydropyridin-3-yl)acetonitrile, or a a pharmaceutically acceptable salt of any of the foregoing compounds.

6. A method of treatment of dementia in mammals, which comprises administering to the sufferer an effective amount of a compound of claim 1 or a pharmaceutically acceptable salt thereof.

* * * * *